(12) United States Patent
Blaustein et al.

(10) Patent No.: US 6,360,395 B2
(45) Date of Patent: Mar. 26, 2002

(54) ELECTRIC TOOTHBRUSH

(75) Inventors: Lawrence A. Blaustein, Moreland Hills; John R. Nottingham, Hunting Valley; John Osher, Moreland Hills; John W. Spirk, Gates Mills; Douglas A. Gall, Westlake, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/766,703

(22) Filed: Jan. 22, 2001

Related U.S. Application Data

(63) Continuation of application No. 09/382,745, filed on Aug. 25, 1999, now Pat. No. 6,178,579, which is a continuation-in-part of application No. 09/236,794, filed on Jan. 25, 1999, now Pat. No. 6,189,693, which is a continuation-in-part of application No. 09/163,621, filed on Sep. 30, 1998, now Pat. No. 6,000,083.

(51) Int. Cl.[7] ............................................. A46B 13/02
(52) U.S. Cl. ........................................... 15/28; 15/22.1
(58) Field of Search .................. 15/22.1, 22.2, 15/22.4, 23, 24, 28, 29

(56) References Cited

U.S. PATENT DOCUMENTS

| | | |
|---|---|---|
| 1,476,433 A | 12/1923 | Vandervoort |
| 1,947,324 A | 2/1934 | Zerbee |
| 2,196,667 A | 4/1940 | Moseley |
| 2,445,635 A | 7/1948 | Poliakoff |
| 2,558,332 A | 6/1951 | Artale |
| 3,242,516 A | 3/1966 | Cantor |
| 3,400,417 A | 9/1968 | Moret |
| 3,775,800 A | 12/1973 | Veneziani |
| 4,156,620 A | 5/1979 | Clemens |
| 4,203,431 A | 5/1980 | Abura et al. |
| 4,397,055 A | 8/1983 | Cuchiara |

(List continued on next page.)

FOREIGN PATENT DOCUMENTS

| | | |
|---|---|---|
| CA | 1191003 | 7/1985 |
| CN | 2223981 | 4/1996 |
| CN | 2324987 | 6/1999 |
| CN | 2393503 | 8/2000 |

(List continued on next page.)

OTHER PUBLICATIONS website: http://www.crest.com/products/toothbrushes/prod_brushes_content_fl.htr (Nov. 2000).

(List continued on next page.)

Primary Examiner—Randall E. Chin
(74) Attorney, Agent, or Firm—Fay, Sharpe, Fagan, Minnich & McKee, LLP

(57) ABSTRACT

An electric toothbrush having an elongated body having a handle portion, a head portion, and an elongated intermediate portion disposed between the handle portion and the head portion. The head portion includes a static bristle portion and a moving bristle portion. The static bristle portion and the moving bristle portion are disposed along a common longitudinal axis relative to the head portion. The head portion and intermediate portion are dimensioned for disposition in a human user's mouth for brushing of teeth. A motor is disposed in the handle portion and operatively connected to the moving bristles for moving the moving bristles.

45 Claims, 10 Drawing Sheets

U.S. PATENT DOCUMENTS

| | | |
|---|---|---|
| 4,420,851 A | 12/1983 | Wiener |
| 4,827,550 A | 5/1989 | Graham et al. |
| 4,845,795 A | 7/1989 | Crawford et al. |
| 4,897,517 A | 1/1990 | Gundlach |
| 4,989,287 A | 2/1991 | Scherer |
| 5,033,150 A | 7/1991 | Gross et al. |
| 5,035,020 A | 7/1991 | Winiewski |
| 5,054,149 A | 10/1991 | Si-Hoe et al. |
| D321,285 S | 11/1991 | Hirabayashi |
| 5,070,567 A | 12/1991 | Holland |
| 5,120,225 A | 6/1992 | Amit |
| 5,142,723 A | 9/1992 | Lustig et al. |
| D329,946 S | 10/1992 | Curtis et al. |
| D330,286 S | 10/1992 | Curtis et al. |
| 5,170,525 A | 12/1992 | Cafaro |
| 5,186,627 A | 2/1993 | Amit et al. |
| 5,226,206 A | 7/1993 | Davidovitz et al. |
| 5,253,382 A | 10/1993 | Beny |
| 5,274,870 A | 1/1994 | Stollman |
| 5,311,633 A | 5/1994 | Herzog et al. |
| 5,341,534 A | 8/1994 | Serbinski et al. |
| 5,353,460 A | 10/1994 | Bauman |
| D352,829 S | 11/1994 | Perry |
| 5,359,747 A | 11/1994 | Amakasu |
| 5,378,153 A | 1/1995 | Giuliani et al. |
| 5,396,678 A | 3/1995 | Bredall et al. |
| 5,404,608 A | 4/1995 | Hommann |
| D358,486 S | 5/1995 | Loew |
| 5,416,942 A | 5/1995 | Baldacci et al. |
| 5,435,034 A | 7/1995 | Bigler et al. |
| 5,461,744 A | 10/1995 | Merbach |
| D364,740 S | 12/1995 | Loew |
| 5,494,252 A | 2/1996 | Amit et al. |
| 5,504,959 A | 4/1996 | Yukawa et al. |
| D370,347 S | 6/1996 | Heinzelman et al. |
| 5,524,312 A | 6/1996 | Tan et al. |
| 5,590,434 A | 1/1997 | Imai |
| 5,617,601 A | 4/1997 | McDougall |
| 5,617,603 A | 4/1997 | Mei |
| 5,625,916 A | 5/1997 | McDougall |
| D391,083 S | 2/1998 | Nicoll |
| 5,726,932 A | 3/1998 | Lee et al. |
| 5,732,432 A | 3/1998 | Hui |
| 5,732,433 A | 3/1998 | Göcking et al. |
| 5,784,743 A | 7/1998 | Shek |
| D397,251 S | 8/1998 | Eguchi et al. |
| D397,252 S | 8/1998 | Allende |
| 5,822,821 A | 10/1998 | Sham |
| D400,713 S | 11/1998 | Solanki |
| 5,836,030 A | 11/1998 | Hazeu |
| 5,839,148 A | 11/1998 | Volpenhein |
| 5,842,244 A | 12/1998 | Hilfinger et al. |
| 5,842,249 A | 12/1998 | Sato |
| 5,850,655 A | 12/1998 | Göcking et al. |
| D403,510 S | 1/1999 | Menke et al. |
| 5,867,856 A | 2/1999 | Herzog |
| D406,464 S | 3/1999 | Yost et al. |
| 5,901,397 A | 5/1999 | Häfele et al. |
| D414,607 S | 10/1999 | Trojnowski et al. |
| 5,996,157 A | 12/1999 | Smith et al. |
| 6,000,083 A | 12/1999 | Blaustein et al. |
| D422,143 S | 4/2000 | Beals et al. |
| D422,144 S | 4/2000 | Harada |
| D428,261 S | 7/2000 | Lee |
| D430,730 S | 9/2000 | Klein |
| D432,312 S | 10/2000 | Blaustein et al. |
| D433,814 S | 11/2000 | Blaustein et al. |
| D434,563 S | 12/2000 | Lim et al. |
| D434,565 S | 12/2000 | Bojar |
| 6,178,582 B1 | 1/2001 | Halm |
| D437,688 S | 2/2001 | Beals et al. |
| 6,189,693 B1 | 2/2001 | Blaustein et al. |
| D440,048 S | 4/2001 | Beals et al. |
| D444,629 S | 7/2001 | Etter et al. |
| D446,941 S | 8/2001 | Kraemer |
| D448,171 S | 12/2001 | Harris et al. |

FOREIGN PATENT DOCUMENTS

| | | |
|---|---|---|
| DE | 27 36 286 | 8/1977 |
| DE | 3406-112 A | 8/1985 |
| DE | 41 39 788 A1 | 6/1993 |
| DE | 296 00 236 U1 | 1/1996 |
| DE | 296 00 255 U1 | 1/1996 |
| DE | 296 13 608 U1 | 8/1996 |
| DE | 296 18 755 U1 | 10/1996 |
| DE | 297 01 302 U1 | 1/1997 |
| DE | 298 21 121 U1 | 11/1998 |
| EP | 0 254 397 | 1/1988 |
| EP | 0 520 985 B1 | 5/1990 |
| EP | 0 537 465 A2 | 9/1992 |
| EP | 0 569606 A1 | 11/1993 |
| EP | 0 990 424 A1 | 4/2000 |
| EP | 1 053 721 A1 | 5/2000 |
| GB | 2 228 861 A | 9/1990 |
| GB | 2 290 224 B | 5/1994 |
| JP | 5-95816 A | 4/1993 |
| JP | HE15-146314 | 6/1993 |
| JP | 5-199917 A | 8/1993 |
| JP | 6-245820 A | 9/1994 |
| KR | 81-001648 | 4/1981 |
| KR | 81-001646 | 10/1981 |
| KR | U1986-0001137 | 6/1986 |
| SE | 324 221 | of 1969 |
| TW | 137856 | 7/1990 |
| TW | 239963 | 2/1995 |
| TW | 239 964 | 2/1995 |
| TW | 253174 | 8/1995 |
| TW | 330411 | 4/1998 |
| WO | 93/20777 | * 10/1993 |
| WO | WO 94/09676 | 10/1993 |
| WO | WO 95/31123 | 11/1995 |
| WO | WO 98/26730 | 6/1998 |
| WO | WO98/46103 | 10/1998 |
| WO | WO 99/12492 | 3/1999 |
| WO | WO 99/65359 | 12/1999 |

OTHER PUBLICATIONS

Sgan–Cohen, Harold D.; Babayof, Itai; Zadik, Dan; Mann, Jonathan, "One Month Evaluation of the Manually Rotating 'Bio–Bright' Toothbrush for Clinical Safety and Efficacy", Department of Community Dentistry, Faculty of Dental Medicine, Hebrew University–Hadassah, Jeruslem, Israel, J Clin Dent 6: pp. 120–123, 1995.

Bader, Herbert I., "Review of Currently Available Battery–Operated Toothbrushes", Compendium Continuing Education in Dentistry, vol. XIII, No. 12, Dec. 1992, pp. 1162–1167.

* cited by examiner

ELECTRIC TOOTHBRUSH

BACKGROUND OF THE INVENTION

This application is a continuation of application Ser. No. 09/382,745, filed Aug. 25, 1999, now U.S. Pat No. 6,178,579 which is a continuation-in-part of application Ser. No. 09/236,794, filed Jan. 25, 1999, now U.S. Pat No. 6,189,693 which is a continuation-in-part of application Ser. No. 09/163,621, filed on Sep. 30, 1998, now U.S. Pat. No. 6,000,083.

The present invention relates generally to electric toothbrushes. More particularly, it relates to an improved battery powered toothbrush.

The benefits of brushing one's teeth using motorized toothbrushes are well known, and motorized movement in toothbrushes has been the subject of much recent innovation and design activity. Also, the commercial market has seen the introduction, over the last several years, of many different types of motorized toothbrushes. However, an examination of the available technology shows a tendency toward increasingly complex, expensive, and non-commercially feasible methods of achieving motorized motions in the bristles and heads of toothbrushes to aid in more effectively cleaning one's teeth.

The commercial marketplace has become divided into two price markets. On the higher priced end are some of these more complex motorized toothbrushes that provide various motions to the bristles and brush head. The lower end of the market has become the province of very simple motorized toothbrushes that only vibrate through the use of an offset weight attached to the motor shafts and which provide very little true additional cleaning benefit with their use, since no vigorous motion is transmitted to the cleaning surface of the brush. The vibrations are also very uncomfortable to the hand and act as a disincentive to brush one's teeth for an adequate time.

Numerous electric toothbrushes have been developed over the years. Some known devices are shown in U.S. Pat. Nos. 5,070,567; 5,186,627; 5,274,870; 5,341,534; 5,378,153; and 5,732,433. The intention of the present invention is to provide a low cost, effective, ergonomically correct, motorized toothbrush wherein the brush includes both a moving circular brush portion and a fixed brush portion. Accordingly it has been considered desirable to develop a new and improved electric toothbrush which would overcome the foregoing difficulties and others while providing better and more advantageous overall results.

SUMMARY OF THE INVENTION

The present invention relates to an electric toothbrush.

More specifically, the electric toothbrush is used in personal hygiene to clean one's teeth and gums using a motorized movement.

In a first preferred embodiment, the electric toothbrush includes an elongated body portion, a brush head attached to a first end of the elongated body portion, a handle attached to a second end of the elongated body portion, and an angled shaft between the brush head and the handle.

The brush head includes a longitudinal axis, a circular or moving portion and a static portion. The circular portion rotates, swivels, gyrates, oscillates or reciprocates about an axis normal to the longitudinal axis of the brush head and is incorporated into the larger brush head. The static portion includes static bristles located on opposite sides of the circular portion. The stiff bristles of the circular portion can De slightly recessed in height from the static bristles. This particular arrangement allows for the circular portion to include stiff bristles which will aid in the deep cleaning and plaque removal process, while the stationary bristles would typically consist of softer bristles, so as not to damage the gums.

The brush head has a more traditional larger brush head shape which permits the user to brush his teeth in the typical manner of an up and down fashion, while a motorized moving portion of the brush head cleans more effectively. The design of the brush head allows for inexpensive manufacture and brings effective motorized toothbrushes within the financial reach of a larger portion of the population.

The angled shaft provides an ergonomic benefit that has not been utilized on a motorized toothbrush. The angle is well known for its ergonomic benefit in permitting easier access into the back recesses of the mouth while still contacting the tooth surface.

The elongated body portion includes a hollow portion. The toothbrush is further comprised of a motor within the hollow portion of the elongated body portion. The motor is operably connected to the moving portion of the brush head for rotating, oscillating or reciprocating the movable bristles on the head. The motor has a longitudinal axis which is coaxial with a longitudinal axis of the elongated body portion.

The hollow portion further includes a simplified gear assembly. The gearing may comprise any of several embodiments. In one embodiment, the gear assembly includes a worm gear, two step gears and a shaft. The motor is operatively connected to the worm gear. The step gears are operatively connected to the worm gear and to each other. The gear assembly delivers sufficient torque and speed, while preserving battery longevity. The first step gear permits a second matching step gear to be offset with respect to a longitudinal axis of the elongated body portion and placed at the desired angle so that the shaft itself can still be straight, thus losing no power or torque through the added friction of a flexible shaft. The shaft is operatively connected at a first end to the offset step gear and at a second end to the moving portion of the brush head.

The body further includes a switch to allow operation of the unit. The switch includes an actuator button and a metal contact. The switch is manually depressed by pressing a molded actuator button down, which presses against a metal contact, completing the circuit, as in a conventional momentary switch. The switch allows continuous operation, through a ramp design, by depressing and sliding the actuator button forward as in a conventional continuous switch. The forward motion, combined with the molded in ramp, causes the actuator button to move downward, pressing against the metal contact, and completing the circuit. By combining these two functions in one switch, the consumer can try the unit and see its operation prior to purchase, and still operate it continuously once out of the package.

The electric toothbrush can further include a battery located within the hollow portion of the elongated body portion. A slidable, snap-on cover is depressed then released from the end of the handle and opens to expose the hollow portion. The battery is then inserted and then the cover is slid into position and snapped into place.

In a second preferred embodiment, the electric toothbrush includes an elongated body portion, a brush head attached to a first end of the elongated body portion, a handle attached to a second end of the elongated body portion, and an angled shaft between the brush head and the handle.

The brush head includes a longitudinal axis, a circular or moving portion, a static portion, a first end and a second end. The first end of the head is located adjacent the first end of the elongated body portion, and the second end is located opposite the first end. The static portion is located at the first end or second end of the head. The circular portion is then located at the opposite end of the head. The moving portion can rotate, swivel, gyrate, oscillate or reciprocate about an axis approximately normal to the longitudinal axis of the brush head and is incorporated into the larger brush head. The circular portion is preferably located at the second end of the brush head to facilitate easier access and cleaning of the back of the user's mouth. The static bristles are located adjacent the circular portion. This particular arrangement allows for the circular portion to include stiff bristles which will aid in the deep cleaning and plaque removal process further in the back of the user's mouth, while the stationary bristles would typically consist of a softer bristle, so as not to damage the gums.

In a third preferred embodiment, the electric toothbrush includes an elongated body portion having opposed first and second ends, a hollow portion and a longitudinal axis, and a head attached to the first end of the elongated body portion. A handle is attached to the second end of the elongated body portion.

An angled shaft is located between the head and the handle. The toothbrush further includes a motor located within the hollow portion of the elongated body portion.

A plurality of gears are located in the hollow portion. The plurality of gears comprises a first gear and a second gear. The motor is connected to the first gear, and the first gear is connected to the second gear.

The toothbrush also includes three swivel arms. The first swivel arm is pivotably connected to one of the gears. The first and second swivel arms are pivotably connected to each other.

A shaft is operatively connected to one of the pair of swivel arms at a shaft first end and operatively connected to the third swivel arm at a shaft second end. The shaft is located within the angled shaft.

The head can further comprise a moving portion and a static portion. The moving portion and the static portion are located adjacent each other. The third swivel arm is connected to the moving portion. The moving portion further comprises a disk which is connected to the third swivel arm.

The moving portion can be located adjacent a first end of the head and the static portion is located adjacent a second end of the head. Alternately, the static portion is located adjacent the first end of the head and the moving portion is located adjacent the second end of the head. The moving portion can also be located at a center of the head with the static portion located on opposite sides of the head.

The shaft moves in a back and forth manner along the longitudinal axis of the elongated body portion.

The first gear rotates about the longitudinal axis and the second gear rotates about an axis normal to the longitudinal axis.

The swivel arms move in a back and forth manner along the longitudinal axis of the elongated body portion.

The moving portion can rotate or oscillate about an axis normal to the longitudinal axis of the head.

Alternately, the moving portion can move in a back and forth manner along the longitudinal axis of the head.

A switch is operably connected to the motor. The switch is depressed to provide momentary operation of the toothbrush and is depressed and slid in a slot in the elongated body portion to provide continuous operation of the toothbrush.

One advantage of the present invention is the provision of an electric toothbrush with a brush head with a traditional larger brush head shape to permit the user to brush teeth in an up and down fashion.

Another advantage of the present invention is the provision of an electric toothbrush which is inexpensive and easy to manufacture.

Another advantage of the present invention is the provision of an electric toothbrush with an angled shaft to permit easier access to the back of the user's mouth.

Still another advantage of the present invention is the provision of an electric toothbrush with a static portion and a circular or moving portion that rotates, swivels, oscillates or reciprocates.

Yet another advantage of the present invention is the provision of a circular portion that rotates or reciprocates or swivels or oscillates which is positioned at the end of the brush head to facilitate easier access to the back of the user's mouth.

Yet still another advantage of the present invention is the provision of an electric toothbrush with a switch which allows momentary operation or continuous operation of the toothbrush.

Another advantage of the present invention is the provision of an electric toothbrush with swivel arms which provide a simplified mechanism for rotating or oscillating the moving brush head.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein.

DETAILED DESCRIPTION OF THE PREFERRED EMBODIMENTS

Figure 1:
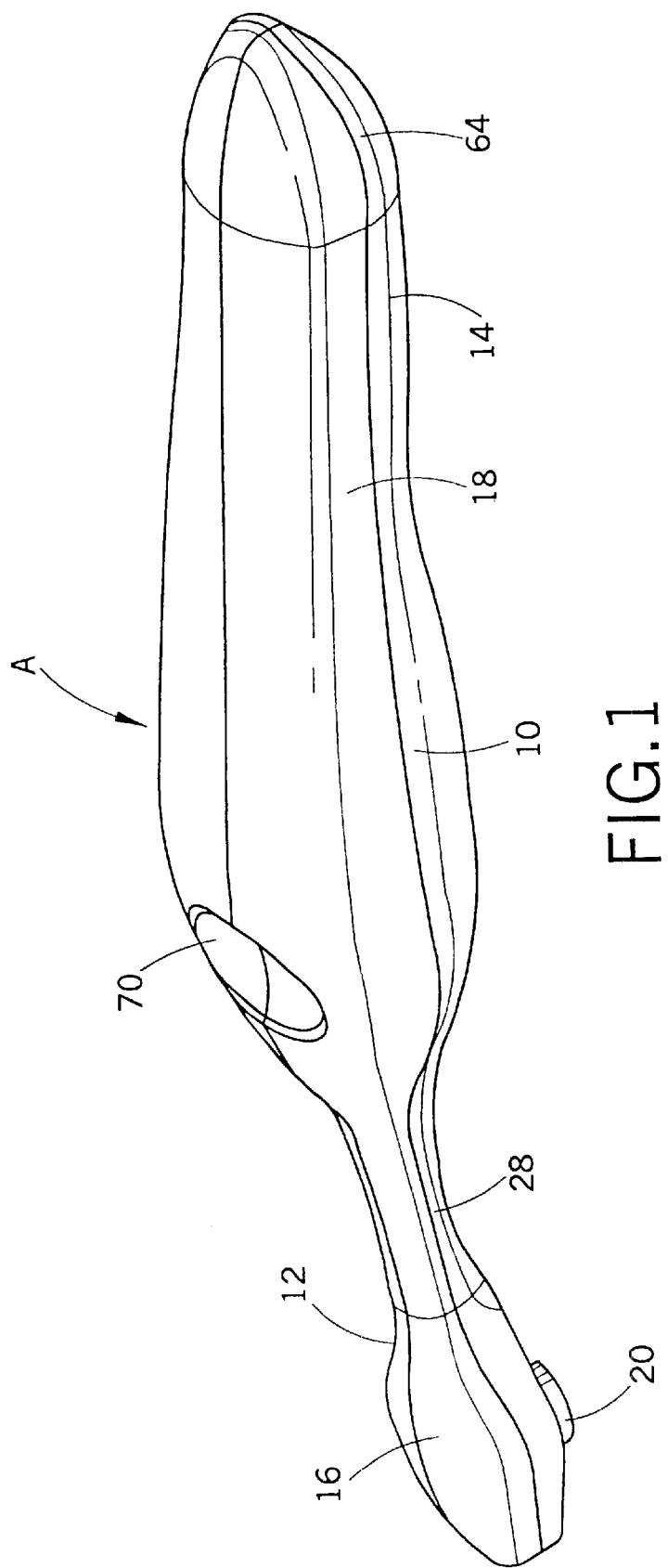
FIG. 1 is a perspective view of the electric toothbrush in accordance with a first preferred embodiment of the present invention.

Referring now to the drawings wherein the showings are for the purposes of illustrating the preferred embodiments of the invention only and not for purposes of limiting same, FIG. 1 shows an electric toothbrush A according to a first preferred embodiment of the present invention. The electric toothbrush can be used for personal hygiene such as brushing one's teeth and gums.

As shown in FIG. 1, the electric toothbrush includes an elongated body portion 10, which has a first end 12 and a second end 14. A head 16 is attached to the first end 12 and a handle 18 is attached to the second end 14.

Figure 2:
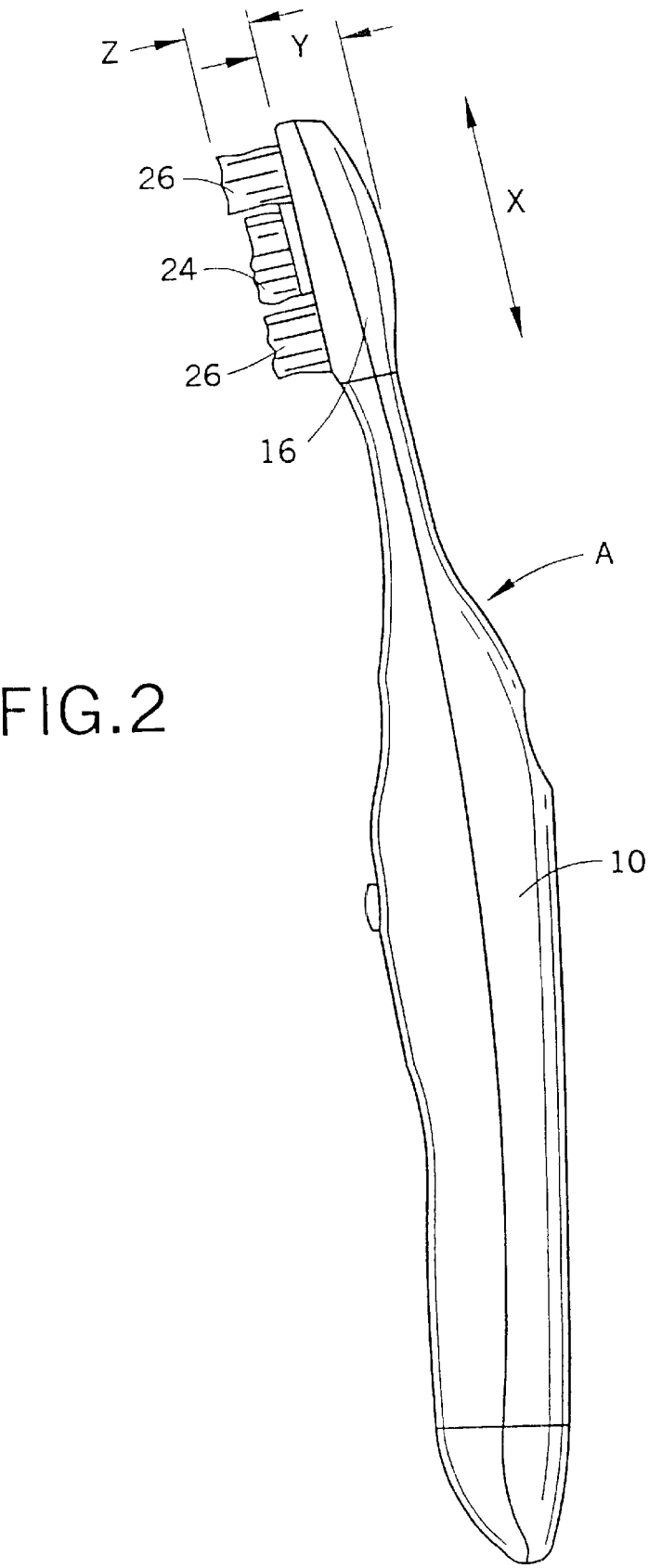
FIG. 2 is a side elevational view of the electric toothbrush of FIG. 1.

The head 16 has a more traditional larger brush head shape which permits the user to brush his teeth in the typical manner of an up and down fashion. As shown on FIG. 2, the length of the head 16, dimension "X", can range from about 0.75 inches to about 1.75 inches. The thickness of the brush head, dimension "Y", can range from about 0.25 inches to about 0.50 inches. The design of the head 16 allows for inexpensive manufacture and assists in bringing effective motorized rotational toothbrushes within the financial reach of a large portion of the population.

Figure 3:
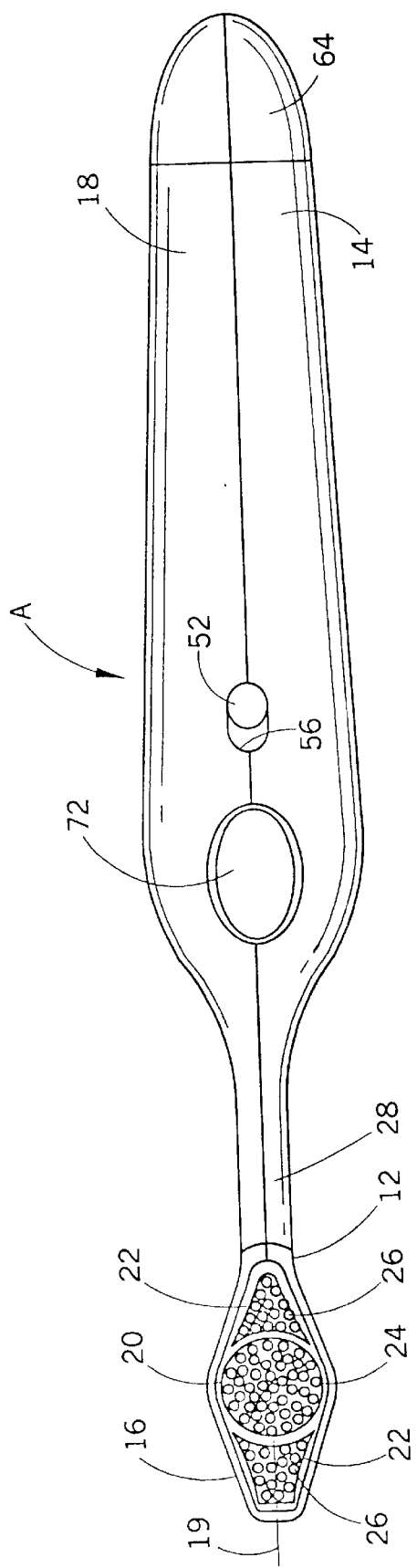
FIG. 3 is a bottom elevational view of the electric toothbrush of FIG. 1.

Referring now to FIG. 3, the head 16 further includes a longitudinal axis 19, a circular or moving portion or brush head 20 and a static portion or brush head 22. The static portion 22 is located on opposite sides of the circular portion 20. The circular portion 20 is located at the center of the brush head 16. The circular portion 20 rotates, swivels, oscillates or reciprocates about an axis approximately normal to the longitudinal axis 19 of the brush head 16. The circular portion 20 may rotate 360° C. or partially rotate or oscillate or reciprocate in a back and forth manner.

The circular portion 20 includes stiff bristles 24. The static portion 22 includes soft bristles 26. The stiff bristles 24 are slightly recessed with respect to the soft bristles 26. The stiff bristles 24 aid in the deep cleaning and plaque removal process, while the stationary soft bristles 26 are softer so as to not damage the gums. The thickness of the bristles, dimension "Z", shown in FIG. 2, can range from about 0.25 inches to about 0.75 inches.

Referring again to FIG. 3, the elongated body portion 10 further includes an angled shaft 28, located between the head 16 and the handle 18. The angled shaft 28 provides an ergonomic benefit that has not been utilized on a motorized toothbrush. The angle is well known for its ergonomic benefit in permitting easier access into the back recesses of the mouth while still contacting the tooth surface.

Figure 4:
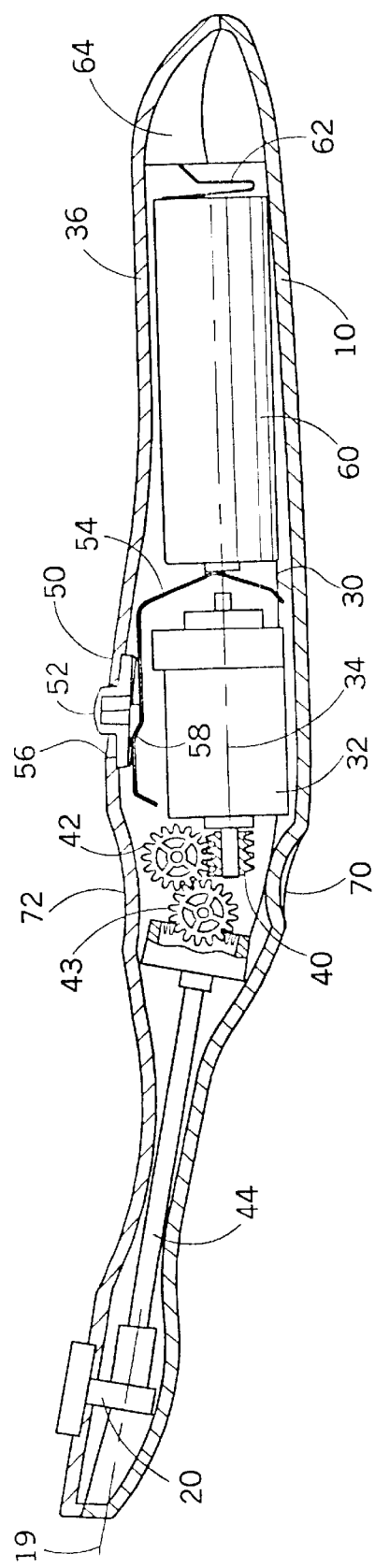
FIG. 4 is a side elevational view in cross section of the electric toothbrush of FIG. 1.
Figure 5:
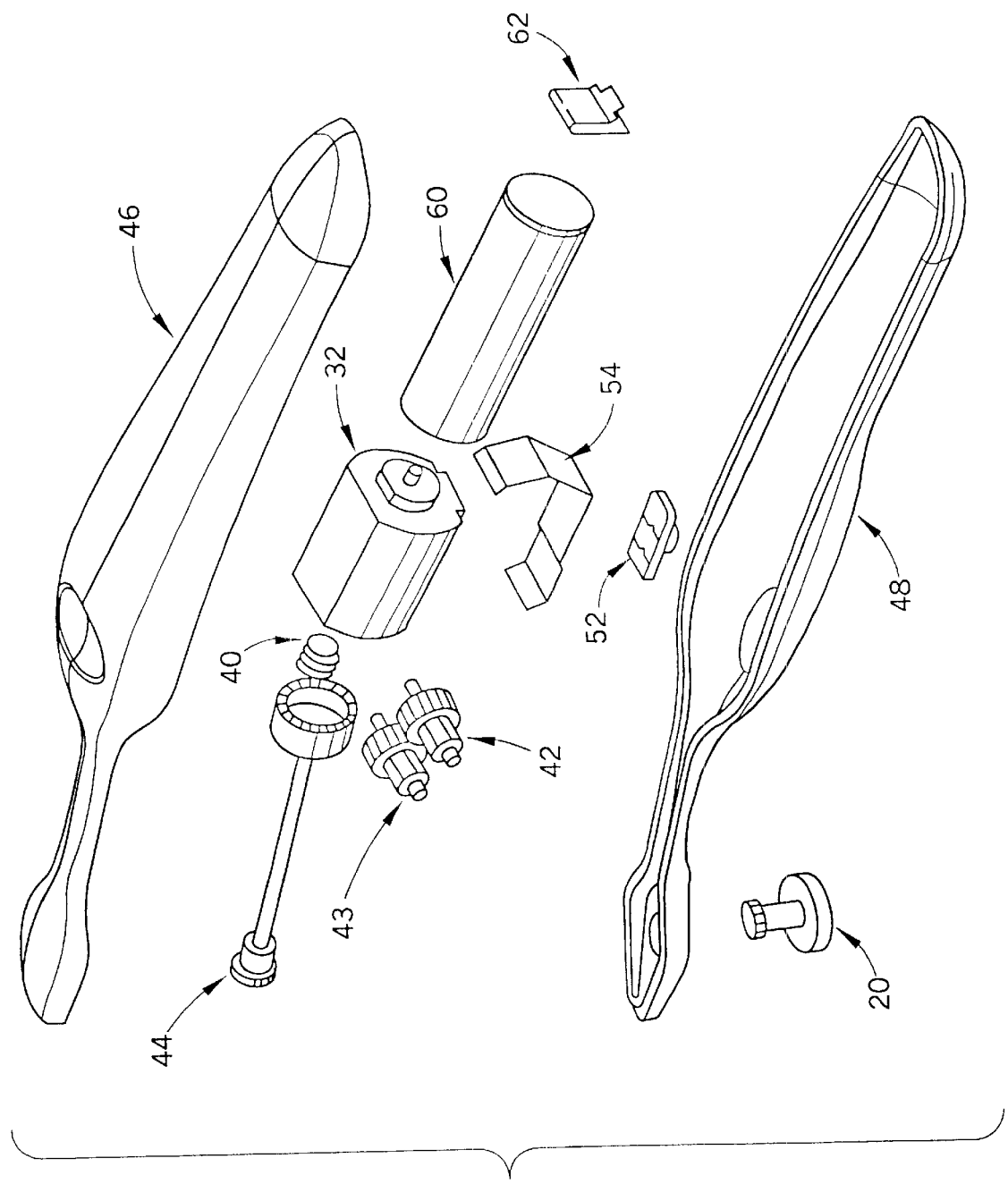
FIG. 5 is an exploded perspective view of the electric toothbrush of FIG. 1.

As shown in FIG. 4 and FIG. 5, the elongated body portion 10 further includes a hollow portion 30 which houses a motor 32. The motor 32 has a longitudinal axis 34 in line with a longitudinal axis 36 of the elongated body portion 10.

To provide power to the circular portion 20 to rotate or oscillate or reciprocate, the motor 32 powers a worm gear 40 and a pair of step gears 42, 43. The motor 32 so is operatively connected to the worm gear 40. Step gear 42 is operatively connected to step gear 43 and the worm gear 40.

Figure 6:
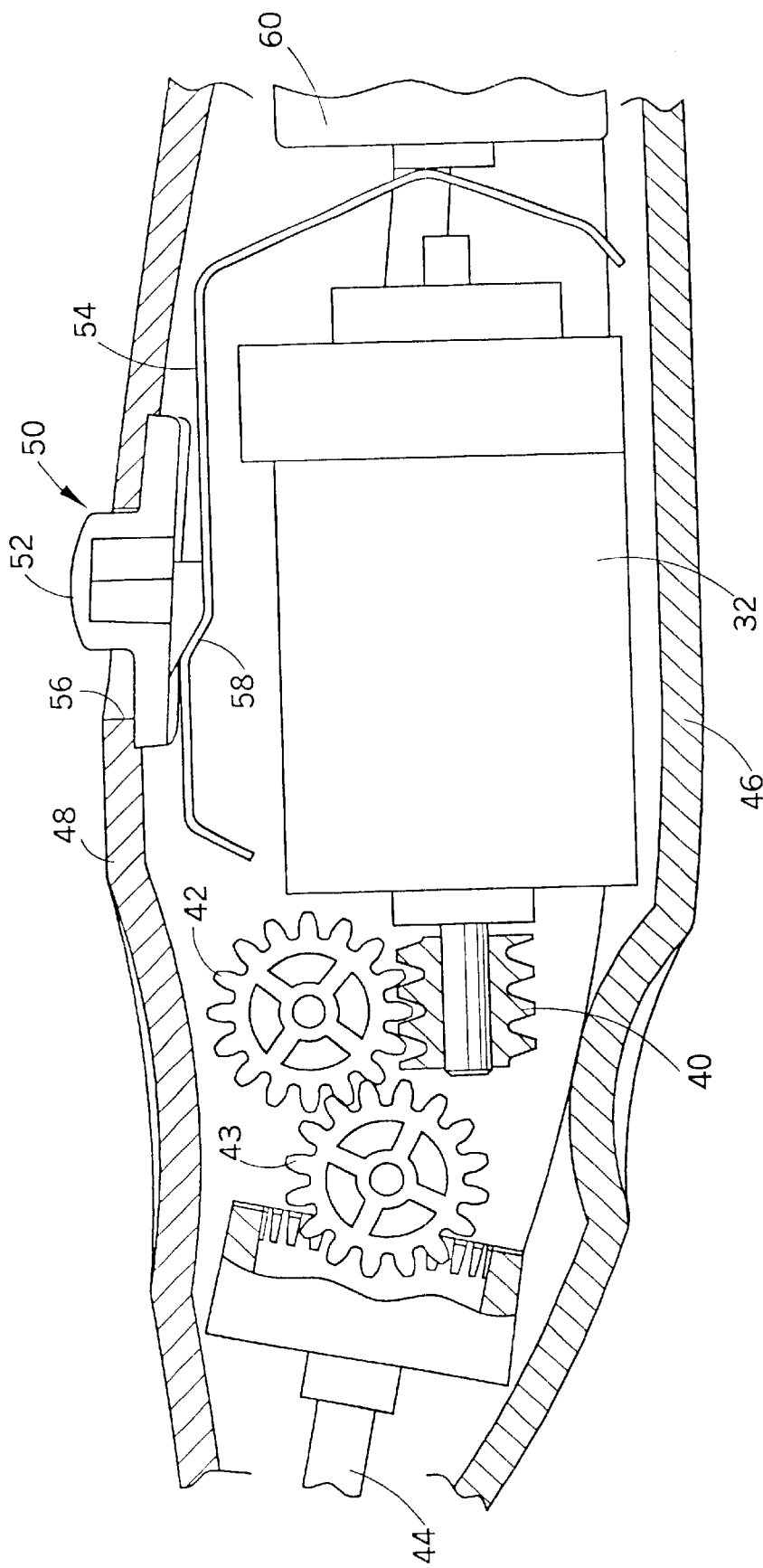
FIG. 6 is an enlarged side elevational view in cross section of the motor and gear assembly of the electric toothbrush of FIG. 1.

As shown in FIG. 4 and FIG. 6, the first step gear 42 permits the matching second step gear 43 to be offset with respect to the longitudinal axis 36 of the elongated body portion 10.

Figure 7:
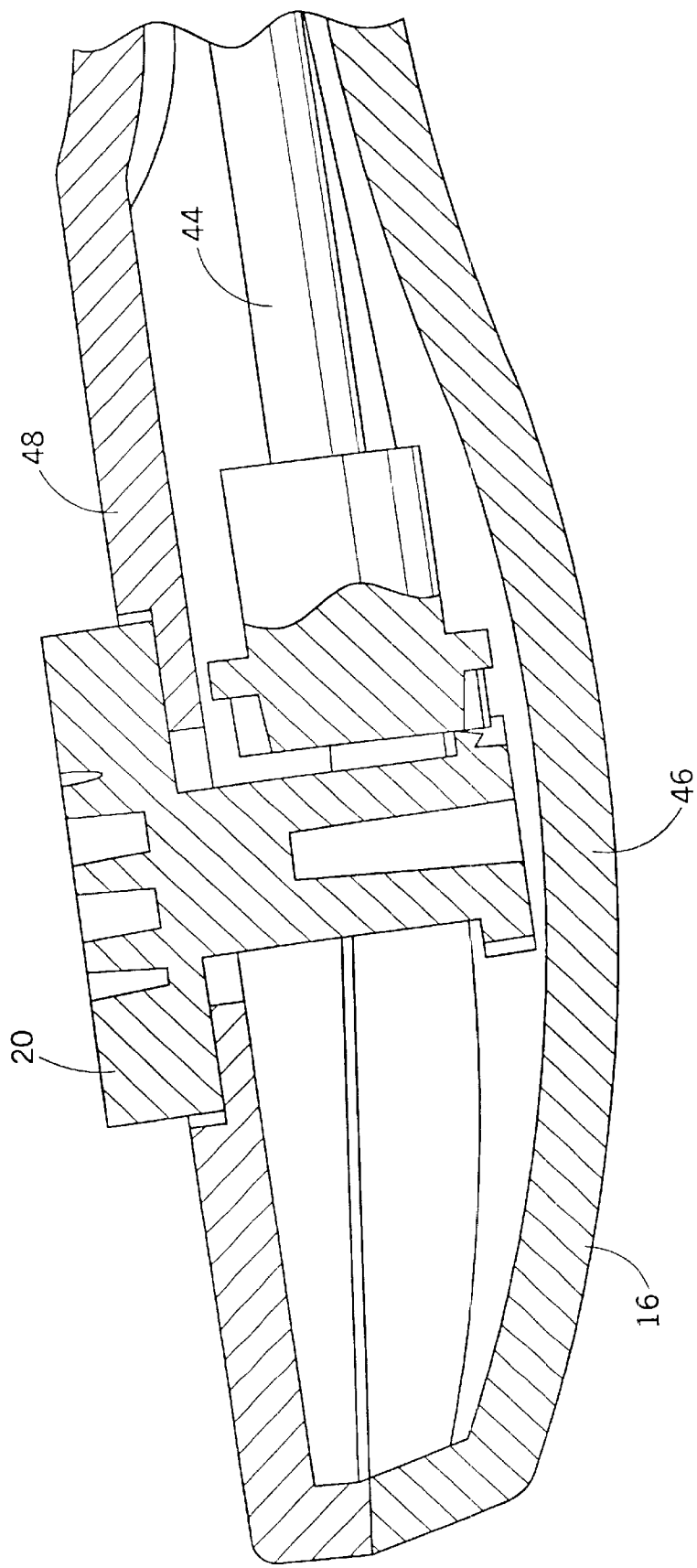
FIG. 7 is an enlarged side elevational view in cross section of the head of the electric toothbrush of FIG. 1.

As shown in FIGS. 4, 6 and 7, a shaft 44 is connected at a first end to the offset step gear 43 and at a second end to the circular portion 20. The second step gear 43 is placed at a desired angle so that the shaft 44 itself can still be straight, thus losing no power or torque through the added function of a flexible shaft.

Referring again to FIG. 5, the motor 32 and gears 40, 42, 43 are housed with an upper housing 46 and a lower housing 48.

Referring again to FIG. 4, a switch 50 is provided to control operation of the electric toothbrush and is operatively connected to the motor 32. The switch 50 includes a molded actuator button 52 and a metal contact 54. The switch 50 is manually depressed by pressing a molded actuator button 52 down, which then presses against a metal contact 54, which completes the circuit and provides momentary operation of the toothbrush. The switch 50 also allows continuous operation through a ramp deign, gliding the button 52 forward toward the head 16 to provide for continuous operation. Moving the button 52 forward, combined with a molded in ramp 58 in the metal contact 54, causes the button 52 to move downward, pressing against the metal contact 54 and completing the circuit. The toothbrush then continuously operates until the button 52 is slid back into an off position toward the handle 18 and the button 52 disengage the metal contact 54.

Figure 8:
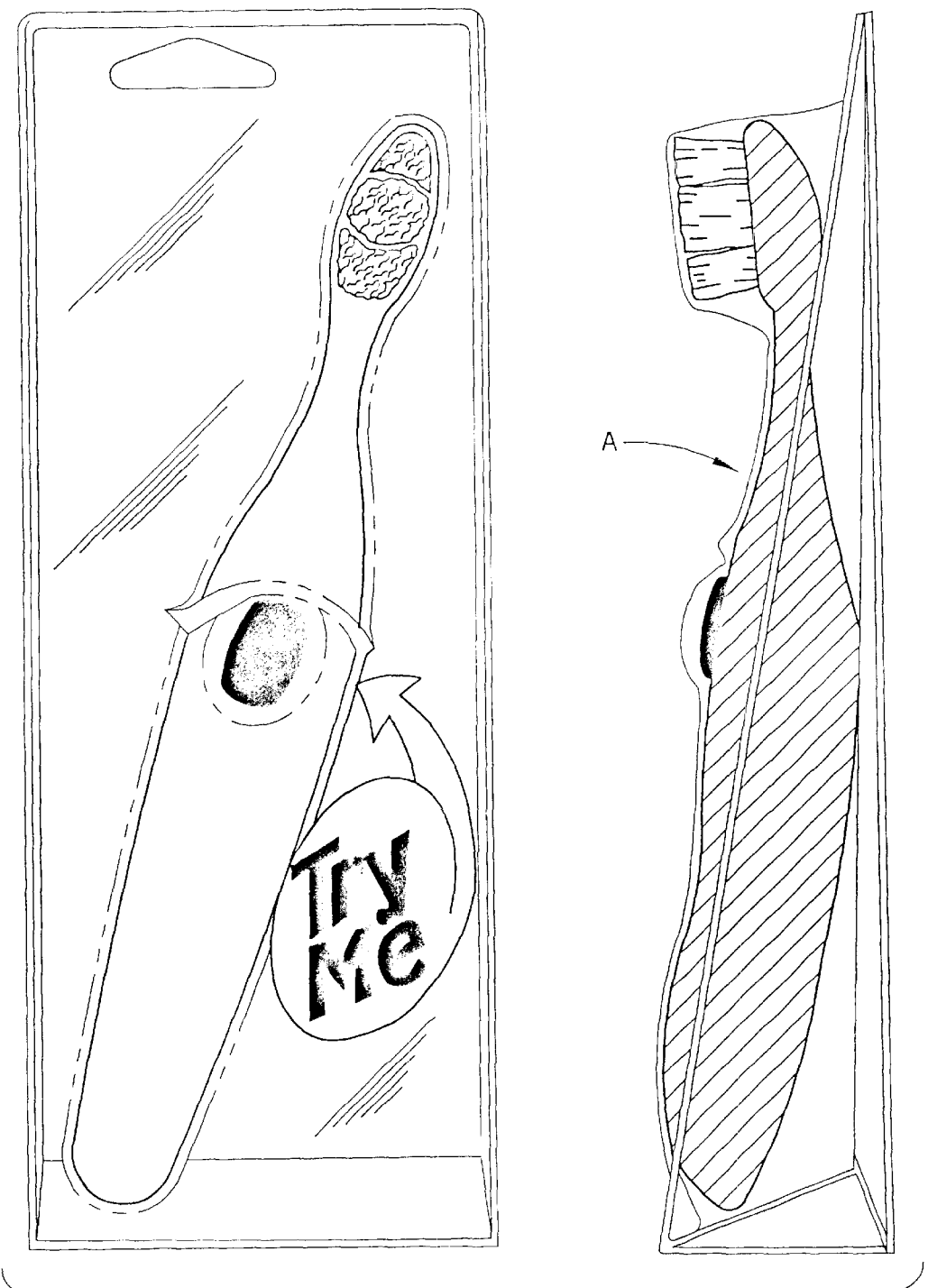
FIG. 8 is a front and side elevational view of the electric toothbrush in packaging.

By combining these two functions in one switch 50, the toothbrush can be packaged in packaging as shown in FIG. 8 where the consumer can depress the button 52 through the packaging and see its operation while still inside the packaging, and then be able to operate it continuously once out of the package. FIG. 8 illustrates one version of the button 52. It should be noted that other sizes and shapes of buttons may be used.

Referring now to FIGS. 4 and 5, a battery 60 is provided within the hollow portion 30 of the elongated body portion 10. A battery terminal or contact 62 is provided for the battery 60. An AA battery can be used as is illustrated in FIG. 4. To install the battery 60 into the hollow portion 30, a slidable snap-on cover 64 is depressed and slid off the end of the handle 18 to expose the hollow portion 30. The battery 60 is inserted, then the cover 64 is slid back on to the housing and snapped into place. The terminal end of the battery 60 is then in contact with the metal contact 54.

If desired, depressions or grip areas 70 and 72 can be molded into the upper and lower housings 46, 48 as shown in FIG. 4. The depressions 70, 72 are used to support a user's thumb and forefinger or other fingers to make using the electric toothbrush easier and more comfortable.

Figure 9:
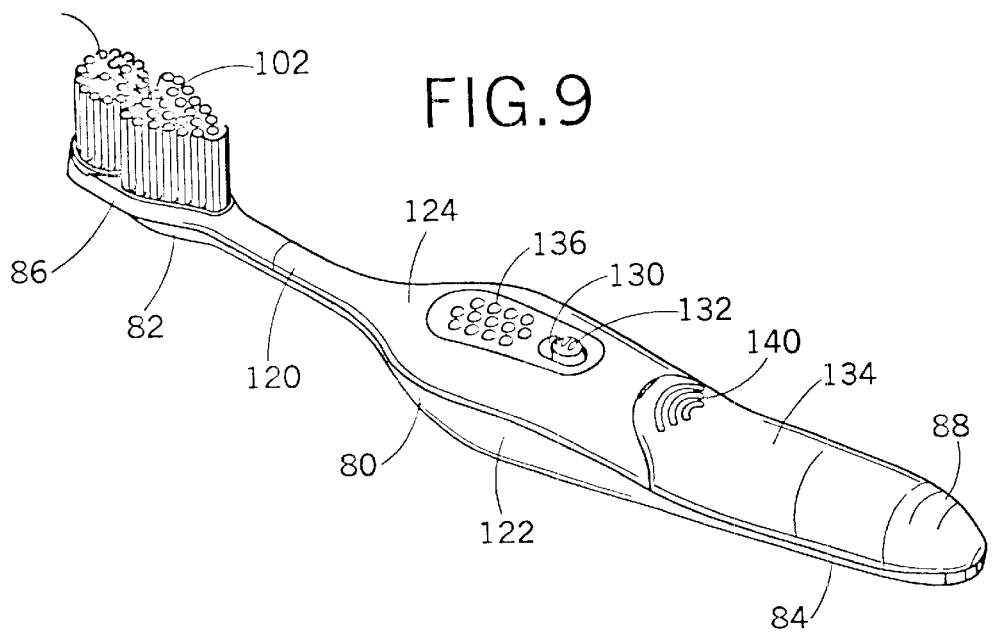
FIG. 9 is a perspective view of the electric toothbrush in accordance with a second preferred embodiment of the present invention.

A second preferred embodiment of the electric toothbrush according to the present invention is shown in FIG. 9.

The electric toothbrush includes an elongated body portion 80 which has a first end 82 and a second end 84. A head 86 is attached to the first end 82 and a handle 88 is attached to the second end 84.

Figure 11:
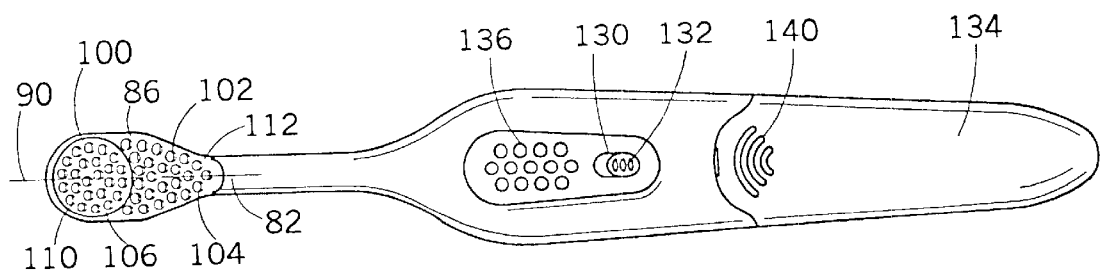
FIG. 11 is a bottom elevational view of the electric toothbrush of FIG. 9.

Referring now to FIG. 11, the head 86 further includes a longitudinal axis 90, a circular or moving portion or brush head 100, a static portion or brush head 102, a first end 104, and a second end 106. The first end 104 is located adjacent the first end 82 of the elongated body portion 80. The second end 106 is located opposite the first end 104. The circular portion 100 is preferably located at the second end 106 of the brush head 86. The static portion 102 is preferably located at the first end 104 of the brush head 86 adjacent the circular portion 100. However, it is to be appreciated that the circular portion 100 and the static portion 102 can be arranged in different orientations. The circular portion 100 rotates, swivels, oscillates or reciprocates about an axis approximately normal to the longitudinal axis 90 of the brush head 86.

The second preferred embodiment also has a worm gear 40 and a pair of step gears 42, 43 as shown in FIGS. 4 and 6. The motor 32 powers the worm gear 40 and the pair of step gears 42,43. The step gear 42 permits the matching step gear 43 to be offset with respect to the longitudinal axis of the elongated body portion 80.

As shown in FIGS. 4, 6, and 7, a shaft 44 is connected at a first end to the offset step gear 43 and at a second end to the circular portion 100. The second step gear 43 is placed at a desired angle so that the shaft 44 can still be straight, thus losing no power or torque through the added function of a flexible shaft.

Referring again to FIG. 9, a switch 130 is provided to control operation of the electric toothbrush and is operatively connected to the motor 32. The switch 130 includes a molded actuator button 132. The switch 130 is manually depressed by pressing a molded actuator button 132 down, which then presses against a metal contact 54, which completes the circuit and provides momentary operation of the toothbrush. The operation of the switch 130 is identical to that shown in FIGS. 4 and 6 and as described for the first preferred embodiment. The switch 130 also allows continuous operation through a ramp design, sliding the button 132 forward toward the head 86 to provide for continuous operation. The toothbrush then continuously operates until the button 132 is slid back into an off position toward the handle 88 and the button 132 disengages the metal contact 54.

Figure 10:
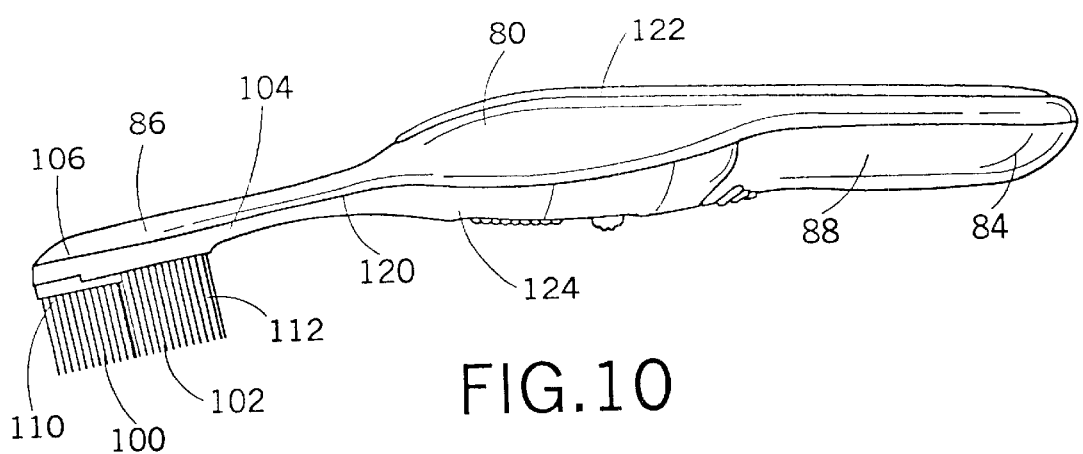
FIG. 10 is a side elevational view of the electric toothbrush of FIG. 9.

As shown in FIGS. 4 and 5 for the first preferred embodiment, the second preferred embodiment also has a battery 60 with a battery terminal or contact 62 provided within the hollow portion 30 of the elongated body portion 80. To install the battery 60 into the hollow portion 30, a slidable snap-on cover 134 (shown in FIGS. 9–11) is depressed and slid of the end of the handle 88 to expose the hollow portion 30. The battery 60 is inserted, then the cover 134 is slid back on to the housing and snapped into place.

If desired, raised grip areas 136 can be molded into the lower housing 124 as shown in FIG. 9 and FIG. 11. The raised portions 136 are used to support a user's thumb and forefinger or other fingers to make using the electric toothbrush easier and more comfortable. Raised portion 140 may also be molded onto the snap-on cover 134 to aid in gripping the cover with one's thumb and removing the cover from the handle 88.

The electric toothbrush of the second preferred embodiment can also be packaged in packaging as shown in FIG. 8 as shown for the first preferred embodiment where the consumer can depress the button 132 through the packaging and see its operation while still inside the packaging, and then be able to operate it continuously once out of the packaging.

Figure 12:
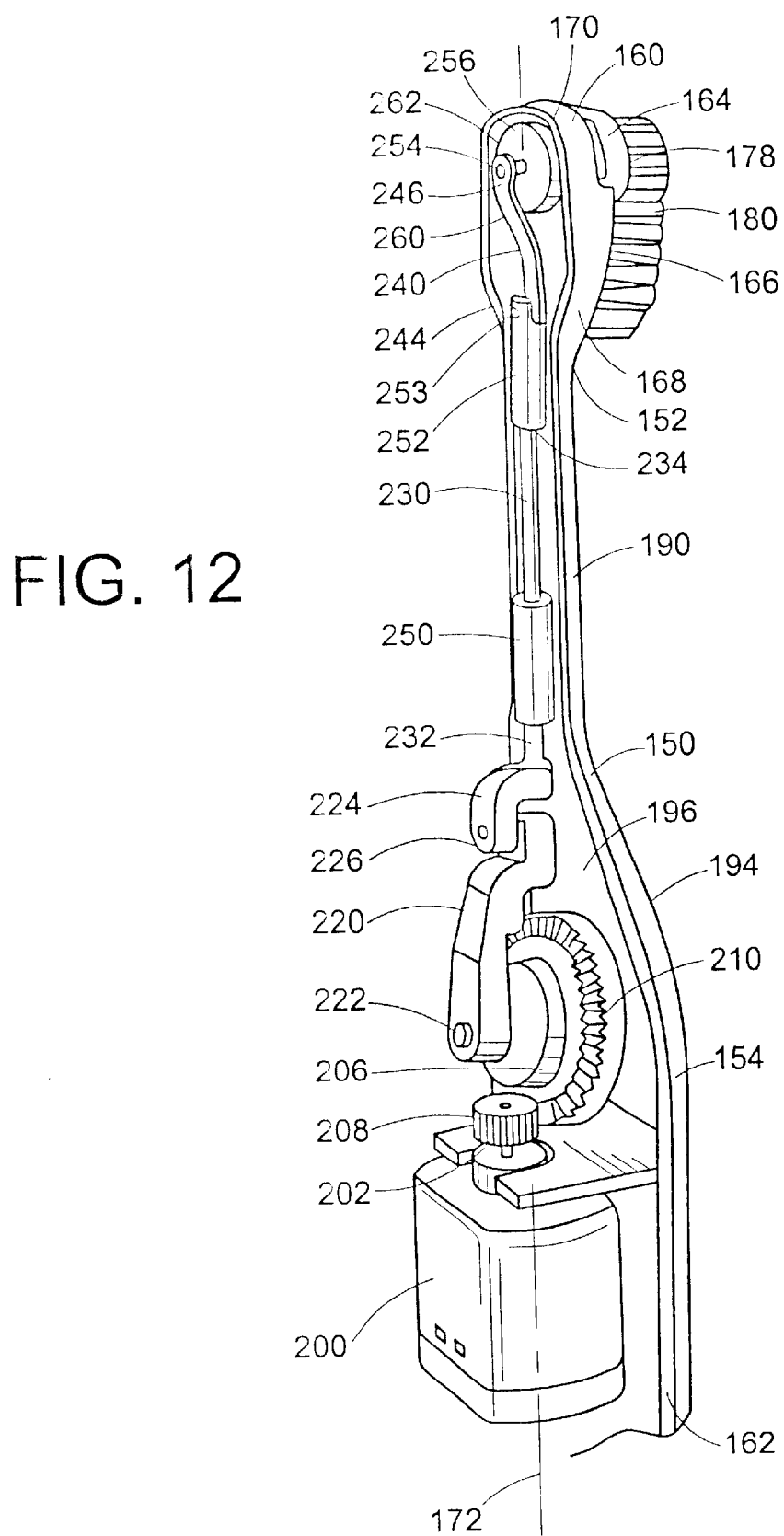
FIG. 12 is a perspective view of the electric toothbrush in accordance with a third preferred embodiment of the present invention.

A third preferred embodiment of the present invention is shown in FIG. 12.

The electric toothbrush includes an elongated body portion 150 which has a first end 152 and a second end 154. A head 160 is attached to the first end 152 and a handle 162 is attached to the second end 154.

The head 160 further includes a moving portion or brush head 164, a static portion or brush head 166, a first end 168, and a second end 170. Am shown in FIG. 12, the moving portion 164 is located adjacent the second end 170. The static portion 166 is shown located adjacent the first end 168. However, it is to be appreciated that the moving portion 164 could be located adjacent the first end 168, and the static portion 166 could be located adjacent the second end 170. Furthermore, the moving portion 164 could be positioned in the center of the brush head with static portions 166 on opposite sides of the moving portion 164 similar to that shown in FIG. 3.

In accordance with this embodiment, the moving portion 164 oscillates about an axis approximately normal to a longitudinal axis 172 of the elongated body portion 150.

The moving portion 164 can include stiff bristles 178. The static portion 166 can include soft bristles 180 which are softer than the stiff bristles. The stiff bristles 178 may be slightly recessed with respect to the soft bristles 180. The stiff bristles 178 aid in the deep cleaning and plaque removal process, while the stationary soft bristles 180 are softer so as to not damage the gums.

The elongated body portion 150 further includes an angled shaft 190, an upper housing 192 (not shown), and a lower housing 194. The angled shaft 190 is located between the head 160 and the handle 162. The angled shaft 190 provides an ergonomic benefit that has not been utilized on a motorized toothbrush.

The elongated body portion 150 of the third preferred embodiment also includes a hollow portion 196 which houses a motor 200. The hollow portion 196 is formed between the upper housing 192 and the lower housing 194. The motor 200 provides power to the moving portion 164 to rotate or oscillate or reciprocate. Power is provided to the motor by battery as shown and described for the first embodiment.

A switch (not shown) can be provided which is similar to switch 130 shown in FIGS. 9 and 11 and which functions as described for the first and second preferred embodiments.

The third embodiment further includes a first gear 202 which is operatively connected to and powered by the motor 200. The first gear 202 rotates about the longitudinal axis 172 of the elongated body portion 150. A second gear 206 is operatively connected to the first gear 202. The second gear 206 is approximately normal to the first gear 202. The second gear 206 rotates about an axis approximately normal to the longitudinal axis 172. Teeth 208 of the first gear 202 mesh with teeth 210 of the second gear 206, thus causing second gear 206 to rotate when first gear 202 rotates.

A first swivel arm 220 is pivotably connected to the second gear 206 via a pin 222 or other fastening device. A second swivel arm 224 is pivotally connected to the first swivel arm 220 via a pin 226 or other fastening device. A shaft 230 is fixedly secured at a shaft first end 232 to the second swivel arm 224. The shaft 230 is pivotably attached at a shaft second end 234 to a third swivel arm 246. The shaft 230 is housed within the angled shaft 190.

The shaft 230 is generally parallel with the longitudinal axis 172.

A guide spacer 250 is located within the angled shaft 190 and surrounds the shaft 230 adjacent the first end 232 of the shaft 230 to minimize lateral movement of the shaft 230. A second guide spacer 252 is located adjacent the second end 234 of the shaft 230 to also minimize lateral movement of the shaft 230. Guide spacers 250, 252 align the shaft 230 within the angled shaft 190 and minimize its movement from side to side within the angled shaft 190.

The third swivel arm 240 has a first end 244 and a second end 246. The third swivel arm 240 is pivotably connected to the second guide spacer 252 at the swivel arm first end 244 via a pin 253. The third swivel arm 240 is connected at the swivel arm second end 246 to the moving portion 164 via a pin 254 or other fastening device. The pin 254 is connected to a disk 256 of the moving portion 164 which is housed within the head 160.

As the first gear 202 rotates, the second gear 206 is rotated, thus moving the first swivel arm 220 in a back and forth circular fashion about the second gear 206 and along the longitudinal axis 172. The first swivel arm 220 also can pivot about the pin 222. The first swivel arm 220 retains its orientation of approximately parallel to the longitudinal axis 172 of the elongated body portion 150 during movement. The second swivel arm 224 pivots with respect to its pin connection 226 with the first swivel arm 220 thus allowing the shaft 230 to oscillate in a back and forth manner toward and away from the brush head with minimal lateral motion.

During operation, the third swivel arm 240 moves back and forth along the longitudinal axis 172 of the elongated body portion 150 along with the shaft 230.

The swivel arm 240 can also pivot or move slightly laterally in a direction perpendicular to the longitudinal axis.

The third swivel arm 240 has an offset arm 260 which is offset from the longitudinal axis 172 and moves the disk 256 of the moving portion 164 in a partially rotating or oscillating motion. As the third swivel arm 240 moves back and forth, the offset arm 260 moves along an outside edge 262 of the disk 256 in a partially rotating or oscillating fashion about an axis which is approximately normal to the longitudinal axis 172. This causes the bristles 178 to also move in a partially rotating or oscillating manner about an axis approximately normal to the longitudinal axis 172.

When the third swivel arm 240 rotates, the disk 256 also rotates about an axis approximately normal to the elongated body portion longitudinal axis 172. The third, swivel arm 240 also retains its orientation of approximately parallel to the elongated body portion longitudinal axis 172 during movement.

If desired, raised grip areas (not shown) can be provided which are similar to raised grip areas 138 and 140 shown in FIG. 9 and FIG. 11 for the second preferred embodiment. The raised grip areas can be molded into the lower housing 194.

The electric toothbrush of the third preferred embodiment can also be packaged in packaging as shown in FIG. 8 as shown for the first preferred embodiment. The consumer can depress a button (not shown) similar to button 132 shown in FIG. 9 and FIG. 11 for the second preferred embodiment through the packaging and see its operation while still inside the packaging, and then be able to operate it continuously once out of the packaging.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. An electric toothbrush comprising;
   an elongated body having a handle portion, a head portion, and an elongated intermediate portion disposed between the handle portion and the head portion and wherein the intermediate portion has a smaller cross-sectional dimension than the handle portion, the head portion including static and moving bristles, wherein all moving bristles are disposed in only a single moving portion that oscillates or rotates, and the static and moving bristles extend in generally the same direction from the head portion, the head portion and intermediate portion being dimensioned for disposition in a human user's mouth for brushing of teeth; and
   a motor disposed in the handle portion and operatively connected to the moving bristles for moving the moving bristles.

2. The electric toothbrush of claim 1 further comprising a gear assembly operatively connected to said motor.

3. The electric toothbrush of claim 1 wherein said moving bristles include stiff bristles include soft bristles.

4. The electric toothbrush of claim 3 wherein said stiff bristles are recessed with respect to said soft bristles.

5. The electric toothbrush of claim 1 wherein the static bristles are disposed at a first end of the head portion and the moving portion is disposed adjacent the static bristles.

6. The electric toothbrush of claim 5 wherein the moving bristles are disposed at a second end of the head portion, the second end being located at a furthest position from the handle portion.

7. The electric toothbrush of claim 1 further including a switch operatively connected to said motor which provides momentary and continuous operation of the toothbrush.

8. The electric toothbrush of claim 1 further comprising a battery located within said handle portion for powering said motor.

9. The electric toothbrush of claim 1 wherein the head portion has a longitudinal axis and the moving portion oscillates or rotates about an axis substantially normal to the longitudinal axis.

10. The electric toothbrush of claim 1 wherein the static and moving bristles are generally parallel to each other.

11. The electric toothbrush of claim 1 wherein the static and moving bristles are oriented substantially perpendicular to a surface of the head portion.

12. The electric toothbrush of claim 1, wherein the static bristles and moving bristles are disposed on a common side of the head portion.

13. The electric toothbrush of claim 1 further comprising a shaft disposed at least partially within the elongated intermediate portion on a longitudinal axis, wherein the shaft is operatively connected to the motor and to the moving portion to cause the moving bristles to rotate or oscillate about an axis approximately normal to the longitudinal axis of the shaft.

14. The electric toothbrush of claim 13 wherein the shaft rotates.

15. The electric toothbrush of claim 13 wherein the shaft reciprocates.

16. The electric toothbrush of claim 1 wherein at least some terminal ends of the static and moving bristles are disposed to form a generally planar cleaning surface.

17. An electric toothbrush comprising:
   an elongated body having a handle portion, a head portion, and a elongated intermediate portion disposed between the handle portion and the head portion and wherein the intermediate portion has a smaller cross-sectional dimension than the handle portion, the head portion including static and moving bristles, the head portion and intermediate portion being dimensioned for disposition in a human user's mouth for brushing of teeth;
   a motor disposed in the handle portion and operatively connected to the moving bristles; and
   wherein all of said moving bristles are disposed in only a single moving portion the rotates or oscillates about an axis substantially parallel to the moving bristles are wherein said static bristles are disposed in a static portion of said head portion and said static portion is adjacent said moving portion.

18. The electric toothbrush of claim 17 wherein the static bristles are disposed at a first end of the head portion.

19. The electric toothbrush of claim 18 wherein the moving bristles are disposed at a second end of the head portion, the second end being located at a furthest position from the handle portion.

20. The electric toothbrush of claim 17 further comprising an elongated shaft disposed at least partially within the intermediate portion and operatively connected at one end to the motor and operatively connected at another end to the moving portion.

21. The electric toothbrush of claim 20 wherein the moving portion rotates or oscillates about an axis approximately normal to a longitudinal axis of the elongated shaft.

22. The electric toothbrush of claim 17 further comprising a gear assembly operatively connected to said motor.

23. The electric toothbrush of claim 17 wherein said moving bristles include stiff bristles and static bristles include soft bristles.

24. The electric toothbrush of claim 23 wherein said stiff bristles are recessed with resect to said soft bristles.

25. The electric toothbrush of claim 17 further including a switch operatively connected to said motor which provides momentary and continuous operation of the toothbrush.

26. The electric toothbrush of claim 17 further comprising a battery located within said handle portion for powering said motor.

27. The electric toothbrush of claim 17 wherein the static and moving bristles are generally parallel to each other.

28. The electric toothbrush of claim 17 wherein the static and moving bristles are oriented substantially perpendicular to it surface of the head portion.

29. The electric toothbrush of claim 17 wherein the static bristles and moving bristles are disposed on a common side of the head portion.

30. The electric toothbrush of claim 17 wherein at least some terminal ends of the static and moving bristles are disposed to form a generally planar cleaning surface.

31. An electric toothbrush comprising:
an elongated body having a handle portion, a head portion, and an elongated intermediate portion disposed between the handle portion and the head portion, the head portion including static bristles and only a single moving bristle portion, wherein the moving portion rotates or oscillates, and at least some static bristles are disposed intermediate the moving bristle portion and the handle portion, the head portion and intermediate portion being dimensioned for disposition in a human user's mouth for brushing of teeth; and
a motor disposed in the handle portion and operatively connected to the moving bristle portion for moving the moving portion.

32. The electric toothbrush of claim 31 wherein at least some terminal ends of the static bristles and the bristles of the moving portion are disposed to form a generally planar cleaning surface.

33. The electric toothbrush of claim 31 further comprising a gear assembly operatively connected to said motor.

34. The electric toothbrush of claim 31 wherein the bristles of the moving portion include stiff bristles and the static bristles include soft bristles.

35. The electric toothbrush of claim 34 wherein said stiff bristles are recessed with respect to said soft bristles.

36. The electric toothbrush of claim 31 further including a switch operatively connected to said motor which provides momentary and continuous operation of the toothbrush.

37. The electric toothbrush of claim 31 further comprising a battery located within said handle portion for powering said motor.

38. The electric toothbrush of claim 31 further including moving bristles and wherein the static and moving bristles are generally parallel to each other.

39. The electric toothbrush of claim 31 further including moving bristles and wherein the static and moving bristles are oriented substantially perpendicular to a surface of the head portion.

40. The electric toothbrush of claim 31 wherein the static bristles and the bristles of the moving portion are disposed on a common side of the head portion.

41. The electric toothbrush of claim 31 further comprising a shaft disposed at least partially within the elongated intermediate portion on a longitudinal axis, wherein the shaft is operatively connected to the motor and to the moving portion to cause the moving portion to rotate or oscillate about an axis approximately normal to the longitudinal axis of the shaft.

42. The electric toothbrush of claim 41 wherein the shaft rotates.

43. The electric toothbrush of claim 41 wherein the shaft reciprocates.

44. The electric toothbrush of claim 31 wherein the static bristles are are disposed at a first end of a head portion and the moving portion is disposed adjacent the static bristles.

45. The electric toothbrush of claim 44 wherein the removing bristles are disposed at a second end of the head portion, the second end being located at a furthest position from the handle portion.

* * * * *

UNITED STATES PATENT AND TRADEMARK OFFICE
CERTIFICATE OF CORRECTION

PATENT NO.    : 6,360,395 B2                                              Page 1 of 1
DATED         : March 26, 2002
INVENTOR(S)   : Blaustein et al.

It is certified that error appears in the above-identified patent and that said Letters Patent is hereby corrected as shown below:

Column 10,
Line 12, before the second instance of "include" please insert -- and said static bristles --.
Line 67, delete "the" and insert therefor -- that --.

Column 11,
Line 1, delete "are" and insert therefor -- and --.
Line 36, delete "it" and insert therefor -- a --.

Column 12,
Line 47, delete "removing" and insert therefor -- moving --.

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,360,395 B2
DATED : March 26, 2002
INVENTOR(S) : Blaustein et al.

It is certified that error appears in the above-identified patent and that said Letters Patent is hereby corrected as shown below:

Column 12,
Line 44, delete the second instance of "are"
Line 45, insert -- bristle -- after "moving"

Signed and Sealed this

Second Day of March, 2004

JON W. DUDAS
*Acting Director of the United States Patent and Trademark Office*